United States Patent [19]

Keller et al.

[11] Patent Number: 5,626,455
[45] Date of Patent: May 6, 1997

[54] ETHYLENE OXIDE CATALYST LOADING DEVICE

[75] Inventors: James S. Keller; David W. Embry, both of Baton Rouge, La.

[73] Assignee: BASF Corporation, Mt. Olive, N.J.

[21] Appl. No.: 600,647

[22] Filed: Feb. 13, 1996

Related U.S. Application Data

[63] Continuation of Ser. No. 190,742, Jan. 27, 1994, abandoned.

[51] Int. Cl.$^6$ ..................................................... B65G 47/18
[52] U.S. Cl. ........................... 414/288; 414/287; 414/299; 414/300; 198/534; 198/550.2
[58] Field of Search ........................................ 414/146, 293, 414/294, 299, 300, 301, 303, 328, 329; 198/540, 550.01, 550.2, 546, 534

[56] References Cited

U.S. PATENT DOCUMENTS

| | | | |
|---|---|---|---|
| 1,473,633 | 11/1923 | Lea | 198/534 |
| 3,608,751 | 9/1971 | Hundtofte. | |
| 3,701,409 | 10/1972 | Gagnon et al. | 198/534 |
| 3,972,686 | 8/1976 | Johnson et al. | 23/288 R |
| 4,332,806 | 6/1982 | Chapman et al. | 33/126.5 |
| 4,402,643 | 9/1983 | Lytton et al. | 414/160 |
| 4,557,637 | 12/1985 | Barclay et al. | 406/153 |
| 4,701,101 | 10/1987 | Sapoff | 414/876 |
| 4,737,269 | 4/1988 | Bischoff | 209/23 |

FOREIGN PATENT DOCUMENTS

| | | | |
|---|---|---|---|
| 96210 | 10/1923 | Germany | 414/288 |
| 1189766 | 11/1985 | U.S.S.R. | 414/300 |
| 1664681 | 7/1991 | U.S.S.R. | 414/299 |

*Primary Examiner*—Frank E. Werner
*Attorney, Agent, or Firm*—Nixon & Vanderhye P.C.

[57] ABSTRACT

A single tube catalyst loading device is provided which consists of a transport belt system, electric motor, and catalyst loading hopper. Using this equipment, it is possible to control the drop rate of catalyst pellets without incurring mechanical damage or breakage of the catalyst. By raising or lowering the hopper section above the transport belt, it is possible to increase or decrease the drop rate of catalyst. Drop rate is the critical parameter in controlling catalyst density within the tubes of an ethylene oxide reactor.

32 Claims, 2 Drawing Sheets ved in the art for an efficient and expeditious method of loading EO catalyst into reactor tubes which prevents damage to the catalyst material and at the same time affords maximum control over the catalyst drop rate and consequently, control over the packing density of the catalyst within the reactor tubes.

ETHYLENE OXIDE CATALYST LOADING DEVICE

This is a continuation of application Ser. No. 08/190,742 filed Jan. 27, 1994, now abandoned.

FIELD OF THE INVENTION

This invention relates to an apparatus and a process for loading ethylene oxide catalyst into multi-tube vertical reactors using maximum control over the catalyst drop rate and consequently, control over the packing density of the catalyst within the reactor tubes, while at the same time completely avoiding or substantially minimizing mechanical damage to the brittle ethylene oxide catalyst.

BACKGROUND OF THE INVENTION

The reaction for producing ethylene oxide (EO) by direct oxidation of ethylene is a highly exothermic reaction. The heat generated in this reaction must be removed as efficiently as possible to prevent a run-away reaction that wastes expensive raw material and produces undesirable by-products. The industry standard is to use small diameter tubes of about ¾ to 2 inches that are on the average 20 to 42 feet in length and upwards of 5000 tubes per ethylene oxide reactor. Each of the tubes is welded to a tube sheet at each end and the entire tube bundle is jacketed and filled with a heat transfer medium, such as a narrow boiling range kerosene or, in high-pressure jacketed vessels, superheated water. Due to the exothermic heat generated by the reaction, the space velocity is maintained at a high rate. It is imperative that the gas flow through the reactor be uniform across the entire catalyst bed. This reaction is highly temperature dependent and must be controlled within a narrow range to provide optimum selectivity.

As part of the ethylene oxide production, a catalyst is utilized. The catalyst is an alumina solid, much in the shape of a thick walled cylinder, about ⅜ inch in length and about 5/16 inch in overall diameter. There is also a 3/16 inch internal bore through the cylinder. The catalyst may also be produced as pellet material (⅜ in.×⅜ in.). For ethylene oxide reactors with smaller diameter tubes, the catalyst will be made in proportionately smaller particles. The EO catalyst is impregnated with metallic silver, and may also contain various fillers.

As the activity of the catalyst begins to decline, the temperature of the reaction is raised to continue to produce ethylene oxide at an economical rate. However, there are limitations to the catalyst life and within a number of years the selectivity declines to where the catalyst must be replaced. The reactor is then opened and the old catalyst is unloaded and the reactor is reloaded with new catalyst.

Upon removal of the old catalyst the metal tubes must be loaded as quickly and efficiently as possible, since the metal tubes must not rust from ambient moisture and air. Iron oxide is an initiator of impurity formation in the direct oxidation of ethylene to ethylene oxide.

Various schemes have been proposed in an attempt to load multiple tubes simultaneously; however, experience over the past thirty years has shown that a single tube loader is often the preferred method. The ethylene oxide catalyst is a silver impregnated alumina particle, much in the shape of a thick-walled cylinder. Previous methods for loading the catalyst have utilized a gravity feed funnel with a single electrical motor driving a mechanical stirrer that kept the catalyst flowing at a certain rate. The disadvantage of this funnel arrangement was the breakage of the catalyst.

There presently exists a need in the art for an efficient and expeditious method of loading EO catalyst into reactor tubes which prevents damage to the catalyst material and at the same time affords maximum control over the catalyst drop rate and consequently, control over the packing density of the catalyst within the reactor tubes.

OBJECTS OF THE INVENTION

It is therefore an object of the present invention to provide an apparatus for use in loading catalyst material into reactor tubes which allows for maximum control over the catalyst drop rate and packing density of the catalyst material.

Another object of the invention is to provide a method for loading catalyst which utilizes the above device.

A further object of the invention is to substantially minimize or eliminate damage to catalyst material during the loading process by the use of an improved catalyst loading apparatus and method.

SUMMARY OF THE INVENTION

These and other objects of the invention are achieved by providing a catalyst loading device, suitable for placing catalyst inside a reactor tube, which has a substantially vertical catalyst loading hopper affixed to a support stand. The support stand further houses a catalyst transport belt and an outlet tube funnel. The catalyst loading hopper has a top open end and a bottom open end, with the top open end having a larger circumference than the bottom open end such that the circumference of the hopper decreases from top to bottom, with the bottom open end of the hopper being positioned above the transport belt. Also provided as part of the apparatus are means for adjusting the distance of the bottom open end of the catalyst loading hopper above the catalyst transport belt. There are also means for powering the catalyst transport belt. The aforesaid outlet tube funnel is positioned downstream from the bottom open end of the hopper for receiving catalyst material moving on the transport belt from the hopper.

Also provided as part of the invention is a method of loading ethylene oxide catalyst material into a reactor tube which utilizes the apparatus according to the various embodiments of the invention.

The special transport belt drive mechanism of the apparatus of the invention will carry ethylene oxide catalyst material from the bottom of the catalyst loading hopper to the outlet tube funnel. With the device and method of the invention the catalyst is not mechanically stirred or agitated which causes mechanical breakage of the catalyst. The drive motor turns the transport belt at a substantially constant speed and by adjusting the height of the catalyst loading hopper above the transport belt, the rate of catalyst pour can be increased or decreased. Setting a number of single tube catalyst loading devices at a particular pouring rate will allow the entire catalyst bed to have a uniform packing density. This uniform packing density of the catalyst is critical to the safe and efficient operation of the ethylene oxide reactor.

DETAILED DESCRIPTION OF THE PREFERRED EMBODIMENT

Figure 1:
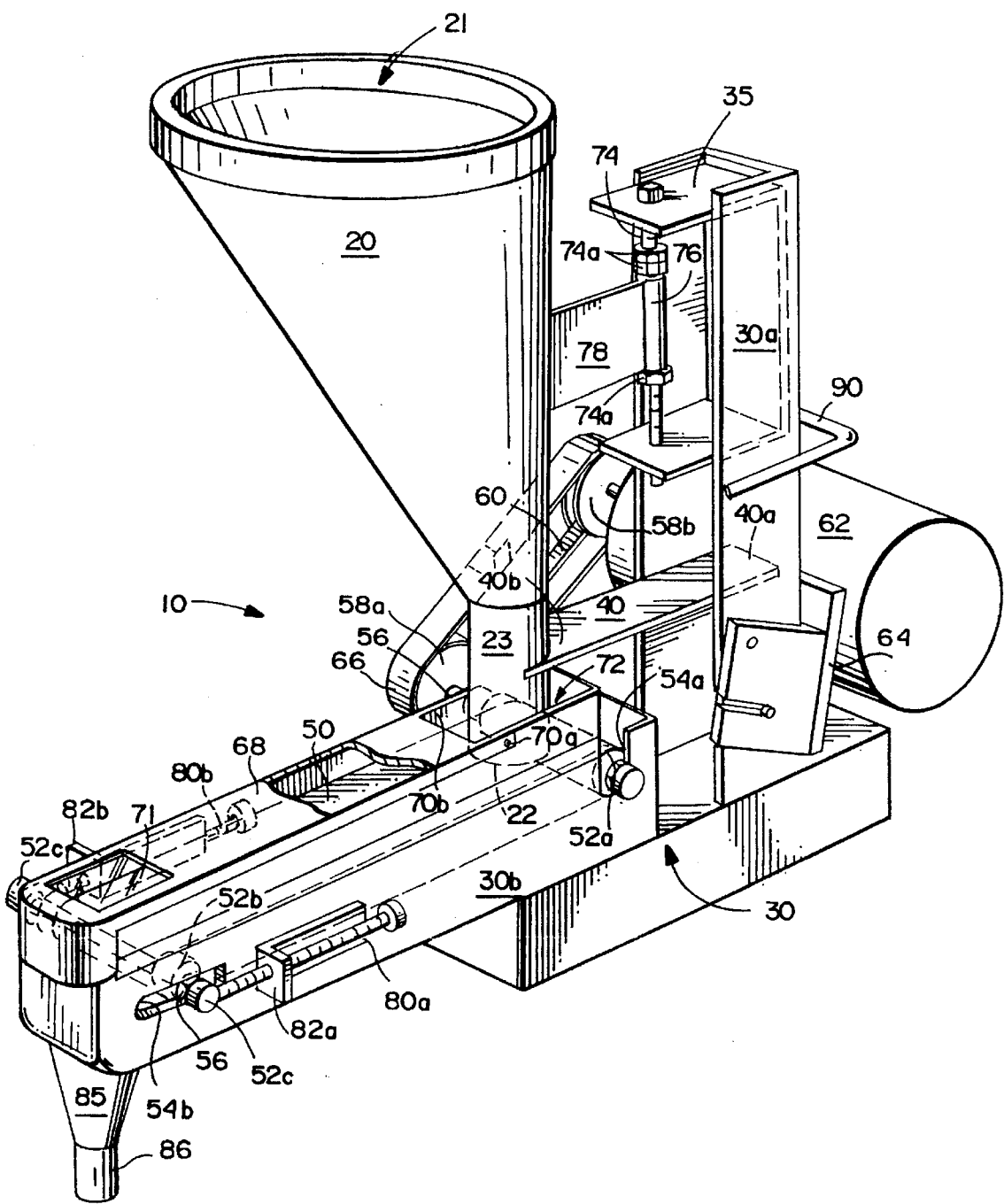
FIG. 1 is a perspective view, partly in section, of an exemplary embodiment of the apparatus according to the present invention.

Referring now to the drawings in which like numerals indicate like components throughout the various embodiments, FIG. 1 is a perspective view of the apparatus of the present invention. A catalyst loading device 10 consists of a catalyst loading hopper 20 to hold an individual bag of catalyst material. As can be seen in FIG. 1, the catalyst loading hopper is substantially vertical or upright, with a top open end 21 and a bottom open end 22. The top open end 21 is larger than the bottom open end such that the catalyst loading hopper 20 decreases in both circumference and diameter from top to bottom.

While it is preferred that the interior of the catalyst loading hopper 20 be substantially conical, other shapes may also be envisioned and are within the scope of the invention. Those skilled in the art will find that the overall shape of the catalyst loading hopper should facilitate the movement of catalyst material downward from the top open end to the bottom open end of the hopper. Especially preferred is the conical shape of the catalyst loading hopper shown in FIG. 1, wherein one side is substantially perpendicular to the imaginary plane below the hopper, while the other side forms an acute angle within the range of about 35° to 75° relative to the aforesaid plane.

The bottom open end 22 of the catalyst loading hopper is preferably formed into a hopper outlet 23. The hopper outlet is a substantially vertical, open hollow cylinder.

While the overall dimensions of the catalyst loading hopper 20 may vary somewhat, it is preferred that the top open end 21 be within the range of about 10 to 18 inches in diameter across, more desirably about 12 to 16 inches, and most preferably about 14 inches in diameter. The diameter of the bottom open end 22 and thus the hopper outlet 23 of the hopper 20 is within the range of about 1½ to 3½ inches, more preferably about 2 to 3 inches, and most preferably about 2½ inches in diameter.

As shown in FIG. 1, the catalyst loading hopper 20 is attached to an upright support stand member 30a associated with the support stand assembly 30. It is highly desirable that the support stand member 30a be substantially rigid. While the loading hopper 20 may be either permanently or removably affixed to the support stand member 30a, it is desirable that the hopper be removably attached thereto by means known in the art. In this way, the catalyst loading hopper 20 can be separated from the support stand member 30a during transport of the catalyst loading device 10. Preferably, a pair of wing nuts (not shown) is utilized to mount the catalyst loading hopper to a U-shaped mounting bracket 35 as part of the support stand member 30a. This configuration will allow the catalyst loading hopper 20 to be separated from the support stand member 30a and then passed through a small man-way (not shown) in the top head of the ethylene oxide reactor. Once inside the reactor, the hopper 20 may be reattached to the mounting bracket 35 with the wing nuts.

There may also be provided as part of the catalyst loading hopper 20 an additional component known as a rigid support brace 40 which radially extends from the hopper 20 so that its terminal end 40a slides within the support stand member 30a, the other end 40b of brace 40 is permanently attached to the hopper 20. As a result, the brace 40 provides lateral support to the catalyst loading hopper 20. The hopper 20 thus be buttressed against the support stand member 30a by means of the rigid support brace 40.

The support stand assembly also includes a support base 30b which houses a catalyst transport belt 50. The transport belt 50 rides on two hollow cylindrical rods 52a, 52b which are in turn positioned inside grooves 54a, 54b inside the support base 30b. A connecting rod 56 connects the cylindrical rod 52a and thus the transport belt 50 to a pulley 58a. A "V" belt 60 rides on pulley 58 A and a second pulley 58b. Pulley 58B in turn is connected to a source of power, which is preferably a 110 V electric motor 62.

The motor 62 can be permanently or removably affixed to the support stand member 30a by means of motor mounting bracket 64. Motive force to turn the catalyst transport belt 50, preferably at a constant speed, is thus supplied by the "V" belt 60, running through the two pulleys 58a, 58b and driven by the 110 volt electric motor 62 attached to the support stand member 30a by means of bracket 64. It is to be understood that other means for supplying motive force to the catalyst transport belt 50 are within the scope of the invention.

Both the catalyst transport belt 50 and the "V" belt 60 are made from rubber, or other synthetic polymer material known in the art. In the configurations shown in FIG. 1, both the transport belt and "V" belt will move in a counterclockwise direction. The length of the transport belt 50 as measured between cylindrical rods 52A and 52B will be between about 10 and 14 inches, desirably between about 11 and 13 inches, and more preferably about 12 inches. The transport belt 50 will be about 2½ to 4 inches wide, more preferably about 3 to 3½ inches wide, and most preferably about 3¼ inches wide. The transport belt 50 will allow for the transport of the catalyst without incurring mechanical damage to the catalyst pellets.

The "V" belt 60 will be about ½ to 1½ inches wide, and about 8½ to 10½ inches long as measured between the respective centers of pulleys 58 A and 58 B.

A "V" belt guard 66 may be utilized to protect the "V" belt 64. It is preferable that if the belt guard 66 is employed, that it completely surround the "V" belt 64.

A transport belt hinged cover 68 may also be utilized to protect the catalyst transport belt 50. The transport belt hinged cover will have first and second substantially linear distal ends. Means are provided to secure the first distal end of the transport belt hinged cover 68 to the support base 30b, such as via cover attachment screws 70a, 701. As the name implies, the hinged cover 68 may be lifted to view catalyst material moving down the transport belt 50.

An optional cover window 71 in proximity to the second distal end of the hinged cover 68 may also be provided for viewing the transport belt 50, and catalyst material moving thereon.

A cover opening 72 in the support base 30b which borders or is juxtaposed next to the hinged cover 68 will accommodate the hopper outlet 23 of the catalyst loading hopper 20. Most preferably, the hopper outlet 23 extends downward inside the cover opening 72 of the transport belt hinged cover 68. In this way, there is unobstructed access to the catalyst transport belt 50 for catalyst pellets moving downward through the hopper outlet 23 and onto the transport belt 50. The cover opening 72 is preferably square or rectangular shaped, with dimensions which will allow the hopper outlet 23 to fit down inside the cover 68. In this way, the cover 68 will not inhibit the flow the catalyst pellets from the hopper 20 onto the transport belt 50. In one preferred embodiment, the cover opening 72 is about 3 inches square. In another embodiment, the cover opening can be about 3 inches in width by about 4 inches in length.

Means are also provided for adjusting the height of the catalyst loading hopper 20 above the transport belt 50. New catalyst pellets will fall by gravity, through the hopper outlet 23 of the catalyst loading hopper 20, which extends through the cover opening 72 of the transport belt hinged cover 68. The rate at which the transport belt 50 will move the catalyst to the outlet tube funnel (hereinafter described) will be adjusted by the height of the hopper outlet 23 above the transport belt 50.

As shown in FIG. 1, the height of the catalyst hopper 20 and thus the hopper outlet 23 may be controlled by adjusting hand screw 74. Hand screw 74 is preferably positioned in a substantially vertical manner through holes provided in mounting bracket 35. Hand screw 74 extends through hollow adjustment rod 76, which in turn is connected to hopper support flange 78 radially extending from the hopper 20 by adjustment nuts 74a. Turning hand screw 74 in one direction will thus raise the hopper 20 and hopper outlet 23 above the transport belt 50. As the hopper 20 is raised, the rigid support brace 40 will slide up along the vertical portion of support stand 30. To lower the hopper 20, the hand screw 74 is turned in the opposite direction. As the name implies, the hand screw 74 may be turned by hand, or may also be configured so as to be turned with a mechanical device such as a wrench, etc.

Since the transport belt 50 will preferably move at a constant speed, the height of the hopper outlet 23 above this belt controls the feed out of the hopper 20. By raising the hopper 20 and increasing the distance above the transport belt 50, a larger opening above the transport belt is produced and more catalyst can move from the catalyst hopper onto the transport belt. This increases the speed by which the catalyst hopper empties and hence decreases the time to pour a tube of catalyst. With each catalyst loading device 10 set at the same pour time a uniform catalyst pouring density is assured across the entire reactor bed.

By turning the hand screw 74, the distance between the hopper outlet 23 and the transport belt 50 will preferably vary within the range of about ¼ inch to 1½ inches. In a more preferred embodiment, the operational distance between the hopper outlet and the transport belt will be between about ½ and 1¼ inches. It is especially preferred that during operation, the height of the hopper outlet above the transport belt be between about ½ and 1 inch.

As heretofore stated, by carefully controlling the height of the hopper outlet 23 above the transport belt 50, the rate at which catalyst will move onto the transport belt can be controlled. The need for additional mechanical implements inside the hopper for stirring or agitating the catalyst material can thus be eliminated. The ability to securely control the drop rate of the catalyst by raising or lowering the hopper outlet will thus have the added benefit of substantially reducing or eliminating the breakage of catalyst as well. This in turn will help ensure that adequate catalyst density inside the reactor tube can also be maintained.

Those skilled in the art may also find that other means for adjusting the height of the catalyst loading hopper 20 above the transport belt 50 to control the drop rate of catalyst onto the transport belt 50 can be utilized in the apparatus of the invention.

Means are also provided for maintaining proper tension, and therefore constant speed of the transport belt 50. Preferably, this is accomplished by means of two belt tension screws, 80a, 80b on corresponding lateral sides of the support stand 30. Belt tension screws 80a, 80b are mounted through belt tension brackets 82a, 82b, respectively, in the support base 30b and are in substantial contact with a pair of circular nuts 52c located in substantial contact with the distal ends of cylindrical rod 52b. Other means for providing the proper tension of the transport belt 50 are also within the scope of the invention.

Also provided as part of the catalyst loading device 10 is an outlet tube funnel 85 positioned "downstream" from the hopper outlet 23 relative to the movement of the transport belt 50. The outlet tube funnel 85 is removably or permanently affixed to the support base 30b, preferably permanently affixed, and is positioned below the plane of the transport belt 50 so as to receive catalyst pellets therefrom. The outlet tube funnel 85 extends downward, and is preferably conically or funnel-shaped, with decreasing diameter in the downward direction.

The outlet tube funnel 85 tapers to form an outlet tube channel 86. The outlet tube channel 86 will fit inside an individual reactor tube RT (not shown in FIG. 1, but see FIG. 2), preferably about ½ inch inside the reactor tube. Catalyst material will thus enter a reactor tube RT via the outlet tube channel 86.

Ease of handling the catalyst loading device 10 is supplied through an optional carrying handle 90 permanently welded to the support stand member 30a.

In addition, there may be means (not shown in the FIGURES) provided as part of the catalyst loading device 10 which can facilitate the vacuuming of excess catalyst dust from the transport belt 50. These means may take the form of one or more attachments on the support stand assembly 30 which can provide access to the transport belt 50. A tygon tube, for example, may be hooked up to the attachment. The tygon tube, in turn, would be connected to a vacuuming source.

Unless otherwise stated, the various heretofore described components of the catalyst loading device 10 may be constructed of aluminum, aluminum alloy, or other light weight metal material known in the art and adaptable for use in the apparatus of the invention.

Figure 2:
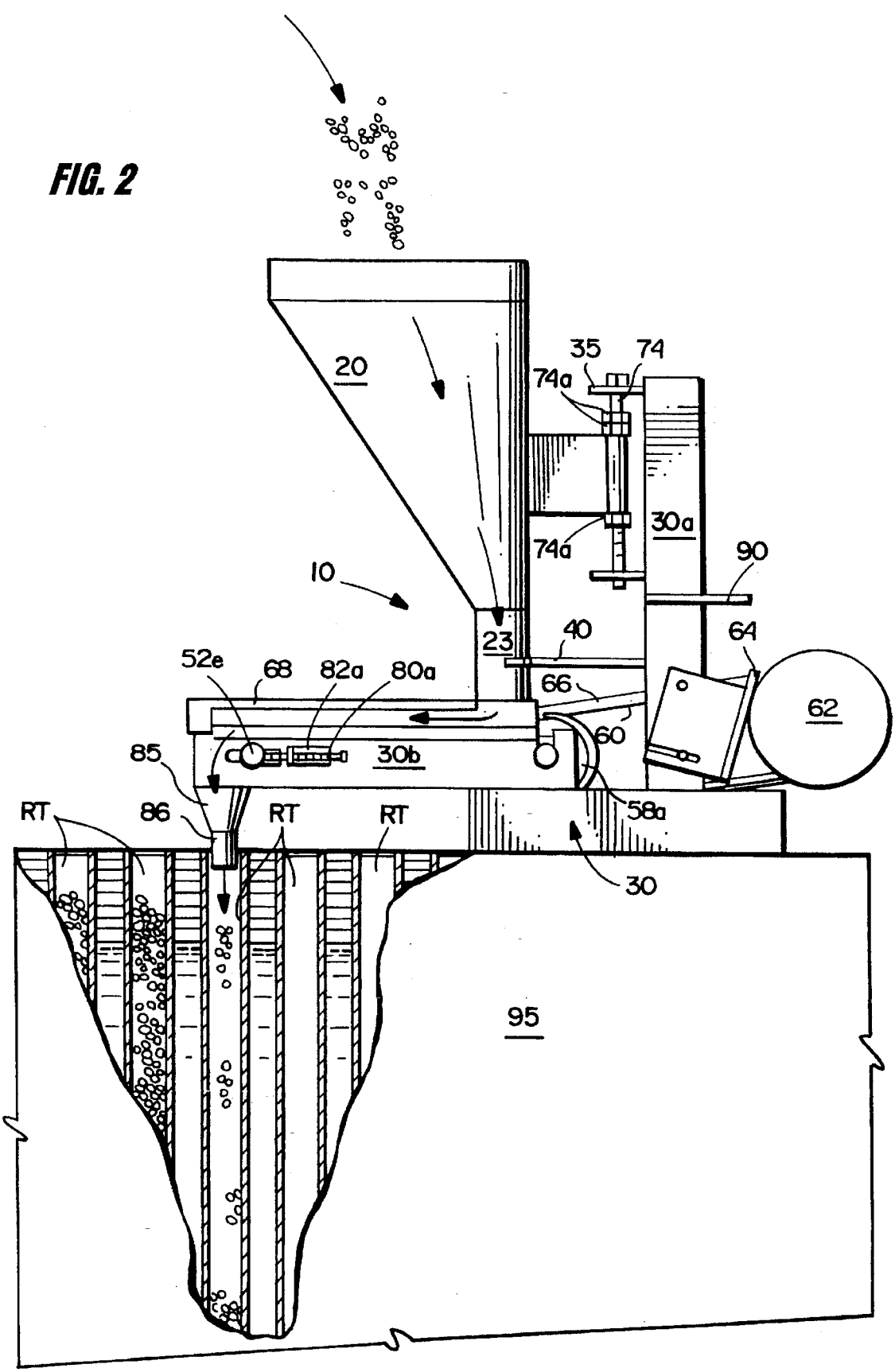
FIG. 2 is a side view of the apparatus of the present invention properly positioned for loading catalyst material inside the head space of an ethylene oxide reactor.

Referring now to FIG. 2, in the use and operation of the catalyst loading device 10 of the present invention, the catalyst loading hopper 20 is first separated from the support stand member 30a to facilitate the passage of the catalyst loading device through the access opening on the top head of the ethylene oxide reactor 95. Reassembling the two major parts is easily accomplished by use of the wing nuts (not shown) and mounting bracket 35 as described previously.

The outlet tube funnel 85 and component outlet tube channel 86 are inserted into the top of an empty tube RT on the top tube sheet of the reactor. With the outlet tube inserted approximately ½ inch into the empty tube RT the single tube catalyst charge funnel sits level on the top tubesheet. In FIG. 2, there is shown a side view of the catalyst loading device 10 according to the present invention properly positioned for loading the catalyst from within the head space of an ethylene oxide reactor 95.

The electric motor 62 is then energized and the transport belt 50 begins moving at a constant speed. An individual bag of catalyst charge is opened and dumped quickly into the catalyst loading hopper 20. The catalyst flows by gravity from the hopper and out of the hopper outlet 23 dropping approximately ½ inch onto the transport belt 50. The transport belt 50 moves the catalyst towards the outlet tube funnel 85 at a constant speed. Falling through the outlet tube channel 86, the catalyst enters and charges the reactor tube RT.

As heretofore set forth, the pouring speed of the catalyst pellets can be increased or decreased by adjusting of the height of the hopper 20 above the transport belt 50 via the handscrew 74. The apparatus of the invention allows the constant movement of solid pellets from the hopper and into the reactor tube without using mechanical stirrers or agitators to keep the catalyst pellets flowing. This prevents mechanical damage to the catalyst pellets.

The pouring speed of the catalyst loading device 10 further determines the packing density of the catalyst pellets as they fall by gravity into the empty reactor tubes RT. A faster pouring speed results in a lower packing density and a slower pouring speed produces a higher packing density on the catalyst. By setting the catalyst loading hopper 20 at the proper height above the transport belt 50, the proper packing density of the catalyst can be achieved. With all of the individual catalyst charging funnels set at the same pouring rate, the overall packing density of the catalyst bed will be substantially uniform. This will facilitate the proper gas flow through the charged tubes of the ethylene oxide reactor.

As the catalyst loading hopper 20 empties, the charging operator can begin preparations to charge the next tube. When the catalyst loading hopper has completely emptied of catalyst, the operator can observe through the cover window 71 that the transport belt 50 no longer has catalyst on it. This confirms the complete charge of catalyst has been successfully loaded into the reactor tube. The operator lifts the outlet funnel 85 of the apparatus from this charged tube and inserts the outlet tube channel 86 into the next empty reactor tube RT. Another individual bag of catalyst is opened and quickly dumped into the catalyst hopper and the entire process repeats. The elapsed time to complete one charge of catalyst from the moment the charge is dumped into the hopper until the last pellet falls into the reactor tube is approximately 90 seconds, but may of course vary slightly. This procedure is repeated until all tubes of the reactor are charged with the new catalyst.

Although this illustrated embodiment is for the charging of catalyst to individual tubes of the ethylene oxide reactor, it will be understood that the principle of operation of the special belt transport and catalyst loading hopper height adjustment system could be scaled up to simultaneously charge a number of empty tubes. At the present time the restriction is in the access to the reactor head space. An ethylene oxide reactor with a removable head could facilitate a much larger apparatus incorporating a number of catalyst hoppers and belt transport systems.

It is also within the scope of the invention that those skilled in the art may utilize the apparatus and device according its various embodiments for the loading of catalyst of various types for the production of many different compounds.

The previous disclosure and description of the invention are both illustrative and explanatory. Various changes in size, shape and materials as well as details of the illustrated construction may be made without departing from the spirit of the invention as set forth in the specification and accompanying claims.

What is claimed is:

1. A catalyst loading device for loading a reactor tube with catalyst comprising:
    (a) a support stand assembly having an upright support stand member, and a support base which includes a proximally located catalyst-receiving section, and a distally located outlet tube funnel for placement at a loading end of a reactor tube;
    (b) a catalyst transport belt connected to said support stand base for transporting catalyst from said catalyst-receiving section to said outlet tube funnel so that said transported catalyst falls by gravity through said outlet tube funnel and into the loading end of the reactor tube;
    (c) a substantially vertical catalyst loading hopper affixed laterally to said upright support stand member, said catalyst loading hopper having a top open end and a bottom open end which is positioned above said catalyst transport belt, said top open end having a larger circumference than said bottom open end such that the circumference of said hopper decreases from top to bottom;
    (d) a hopper adjustment assembly for vertically adjusting said bottom open end of said catalyst loading hopper relative to said catalyst transport belt at said catalyst-receiving section of said housing to establish a distance between said bottom open end of said catalyst loading hopper and said catalyst transport belt to thereby control catalyst feed rate into the reaction tube by said catalyst transport belt;
    (e) a motor assembly connected operatively to said catalyst transport belt for providing motive power to said catalyst transport belt, wherein
    (f) said hopper includes a rigid support brace having one end fixed to said hopper and another end bearing against said support stand, said support brace radially extending from said hopper between said one and another ends thereof so that said another end slides along said upright support stand member during vertical adjustments of said hopper by said hopper adjustment assembly to provide lateral support thereby to said hopper.

2. The device as claimed in claim 1, wherein said catalyst loading hopper is removably affixed to said support stand.

3. The device as claimed in claim 1, wherein said motor assembly includes a motor, first and second pulleys, and a drive belt mounted on said first and second pulleys, wherein said second pulley is connected operatively to said motor.

4. The device as claimed in claim 3, wherein said catalyst transport belt includes first and second cylindrical rods, and further wherein said second cylindrical rod is connected to said first pulley.

5. The device as claimed in claim 4, wherein said support base includes first and second grooves, and wherein said first and second cylindrical rods are seated within said first and second grooves, respectively.

6. The device as claimed in claim 4, further comprising a belt-tensioning assembly for adjusting tension of said catalyst transport belt, said belt-tensioning assembly including first and second tension screws which are operatively connected to one of said first and second cylindrical rods.

7. The device as claimed in claim 6, wherein said belt-tensioning assembly includes mounting brackets positioned on opposite sides of said catalyst transport belt, and wherein said first and second tension screws are mounted in said mounting brackets.

8. The device as claimed in claim 1, wherein said hopper adjustment assembly includes a hand screw.

9. The device as claimed in claim 8, wherein said hopper includes a radially extending hopper support flange, and said support stand member includes a mounting bracket which receives a terminal end of said hopper support flange, and wherein said hand screw operatively couples said terminal end of said hopper support flange to said bracket.

10. The device as claimed in claim 1, wherein said bottom open end of said catalyst loading hopper tapers substantially vertically downward to form a hopper outlet above said transport belt.

11. The device as claimed in claim 1, further comprising a belt-tensioning assembly for adjusting tension of said catalyst transport belt.

12. The device as claimed in claim 1, further comprising a transport belt cover which covers said catalyst transport belt.

13. The device as claimed in claim 12, wherein said transport belt cover has first and second substantially linear distal ends, said first distal end being hinged to said support stand assembly, said second distal end having a window for viewing catalyst moving along said transport belt and downward through said outlet funnel.

14. The device as claimed in claim 13, wherein said outlet funnel tapers to form a outlet tube channel.

15. The device as claimed in claim 14, wherein said first distal end of said transport belt cover is spaced from said upright support stand member so as to define an opening sized and configured to receive said bottom open end of said hopper at said proximally located catalyst-receiving section of said support stand assembly.

16. The device as claimed in claim 1, wherein said support brace is substantially parallel to said catalyst transport belt.

17. The device as claimed in claim 1, wherein said catalyst loading device is made from light weight metal material.

18. The device as claimed in claim 1, wherein said catalyst material is ethylene oxide catalyst.

19. A device for transporting particulate material comprising:
a support stand assembly including a generally horizontally disposed support base having a particulate material receiving section and a particulate material discharge section, and an upright support stand member fixed to said support base;
an endless transport belt assembly connected to said support base for transporting the particulate material between said receiving and discharge sections of said support base;
a loading hopper having an upper hopper inlet to allow particulate material to be introduced thereinto, and a lower hopper outlet to allow particulate material to be discharged therefrom; and
a hopper mounting assembly for mounting the hopper laterally of said upright support stand member so that said hopper outlet is in juxtaposed relationship to said particulate material receiving section of said support base, wherein said hopper mounting assembly includes,
  (i) a hopper support bracket radially extending between said hopper and said upright support stand member;
  (ii) a hopper adjustment assembly which connects said hopper support bracket to said upright support stand member for vertically moving said hopper so as to permit vertical height adjustments of said lower hopper outlet relative to said transport belt at said particulate material receiving section to thereby control discharge rates of the particulate material from the transport belt at said discharge section; and
  (iii) a lateral support brace positioned below and substantially parallel to said radially extending support bracket, said lateral support brace having a proximal end rigidly connected to said hopper and an opposite distal end in sliding contact with said upright support member so as to buttress said hopper against said upright support member.

20. The device of claim 19, wherein said support stand member includes a U-shaped mounting bracket which receives a terminal end of said hopper support bracket, said adjustment assembly connecting said terminal end of said hopper support bracket to said U-shaped mounting bracket.

21. The device of claim 19 or 20, wherein said adjustment assembly includes an adjustment screw.

22. The device of claim 19, wherein said hopper includes a generally conical upper section which includes said hopper inlet, and a generally cylindrical lower section which includes said hopper outlet.

23. The device of claim 19, wherein said support base includes a belt cover which covers said transport belt.

24. The device of claim 23, wherein said belt cover has one end which defines an opening in which said hopper outlet is disposed.

25. The device of claim 24, wherein said belt cover has another end opposite to said one end which is positioned over said discharge section of said support base.

26. The device of claim 25, wherein said one end of said belt cover is pivotally attached to said support base to allow said another end to be pivotally raised from said discharge section of said support base.

27. The device of claim 26, wherein said another end of said belt cover includes a window to permit visual inspection of said discharge section of said support base.

28. The device of claim 19, wherein said support base includes a discharge funnel member depending from said support base at said discharge section thereof.

29. The device of claim 19, wherein said transport belt assembly includes an endless belt, and a motor operatively coupled to said endless belt for moving said endless belt to transport the particulate material between said particulate material receiving and discharge sections of said support base.

30. The device of claim 29, wherein said transport belt assembly includes a pair of pulleys, one said pulley being connected to said motor and another said pulley being connected to said endless belt, and a drive belt interconnecting said pulleys so as to transfer power from said motor to said endless belt.

31. The device of claim 29, wherein said transport belt assembly includes a belt-tensioning assembly operatively coupled to said endless belt to allow tension adjustment of said endless belt.

32. The device of claim 31, wherein said belt-tensioning assembly includes a tension-adjustment bolt.

* * * * *